(12) United States Patent
Bae et al.

(10) Patent No.: US 7,273,967 B2
(45) Date of Patent: Sep. 25, 2007

(54) SWEET POTATO MADS-BOX PROMOTER DIRECTING HIGH LEVEL EXPRESSION IN PLANT STORAGE ROOT

(75) Inventors: Jung Myung Bae, Seoul (KR); Seol Ah Noh, Seoul (KR); Man Sup Kwak, Seoul (KR); Jeong Sheop Shin, Seoul (KR); Haeng Soon Lee, Daejeon (KR)

(73) Assignee: Korea University Industry & Academy Cooporation Foundation

( * ) Notice: Subject to any disclaimer, the term of this patent is extended or adjusted under 35 U.S.C. 154(b) by 0 days.

(21) Appl. No.: 11/153,023

(22) Filed: Jun. 15, 2005

(65) Prior Publication Data

US 2006/0048246 A1    Mar. 2, 2006

Related U.S. Application Data

(63) Continuation of application No. PCT/KR2004/003052, filed on Nov. 24, 2004.

(30) Foreign Application Priority Data

Aug. 25, 2004   (KR) ............... 10-2004-0067290

(51) Int. Cl.
   *C12N 15/82*   (2006.01)
   *C12N 15/70*   (2006.01)
   *A01H 5/00*    (2006.01)

(52) U.S. Cl. .............. 800/287; 435/320.1; 435/419; 536/24.1; 800/298

(58) Field of Classification Search .......... None
   See application file for complete search history.

(56) References Cited

U.S. PATENT DOCUMENTS 5,436,393 A    7/1995  Rocha-Sosa et al. ........ 800/205
6,392,122 B1   5/2002  Clendennen et al. ....... 800/287
2003/0167518 A1  9/2003  Yeh et al. .................. 800/279
2003/0177536 A1  9/2003  Gundler et al. ............ 800/288
2004/0255349 A1  12/2004  Takatsuji et al. .......... 800/286

FOREIGN PATENT DOCUMENTS

KR    2001-51095    6/2001

OTHER PUBLICATIONS

Ellis et al., (1987) Maize adh-1 promoter sequences contrl anerobic regulation: addition of upstream prmoter sequences from Constitutive genes is necessary for expression in tobacco. EMBO J 6:11-16.*
Isolation of MADS-box genes from sweet potato (*Ipomoea batatas* (L.) Lam.) expressed specifically in vegetative tissues, S.H. Kim et al., Plant Cell. Physiol., Mar. 2002, vol. 43(3), pp. 314-322.
High-level expression of tuberous root storage protein genes of sweet potato in stems of plantlets grown in vitro on sucrose medium, T. Hattori et al., Plant Mol. Biol., Apr. 1990, vol. 14(4), pp. 595-604.
Pyk 10, a seedling and root specific gene and promoter from *Arabidopsis thaliana*, I. Nitz et al., Plant Science., Jul. 2001, vol. 161(2), pp. 337-346.
International Search Report dated Feb. 25, 2005, 4 pages.

* cited by examiner

*Primary Examiner*—Russell P. Kallis
*Assistant Examiner*—Brendan O. Baggot
(74) *Attorney, Agent, or Firm*—Tuchman & Park LLC

(57) ABSTRACT

The present invention relates to a promoter directing high levels of expression of a gene in plant storage roots, derived from the sweet potato MADS-box gene, a vector directing high levels of expression of a gene in plant storage roots comprising the same and a transient assay method expressing a foreign gene transiently in plant storage roots using the same vector. The promoter according to the present invention can induce high levels of expression particularly in plant storage roots. Therefore the present invention is very useful for the development of transgenic plants to produce valuable materials in large quantities in plant storage roots.

23 Claims, 7 Drawing Sheets

-2801
GGCTGGTTTCTAAGACATTTTTTGGTTTAATCCAAACCTAATTACAAATATTCCCAACAAGATCGAATGATC
TATGGCTACAAACCCTATCCCAACAAAAAACTACATTTAGTACATCAAATTAAGTGGCATGATTATTTTATT
TTGTTCGACAAAGTAGCATCAAATAAACTACAAAAAAAACTACATCATTACAAAAAGACTAATTATCAGGCA
TCAATGTTAGTATATGGGAGGTGGTGGGTTCGAGCCTCAGTGGAGGCGTTGCTGTCTCTTTGTTCTTCAGT
AGGTTGAGAGAGTAATTTATGAACAGATACTACACTGTAATAGAGTCAGTAGCAATCAAAAAAAAATTTGTT
TTAATAATATCCTAATATTATATTTTTCTAACCAGTACTATGCTTTCGGCTTTCCAGAAGGCAGAAGCCTAA
AAAATTCAATTAAGTTTATAAACTTTAATCCACTTGTTTGAGTAATTGAGTATCTTTCAGAACGGTTGTAG
ATTTAGGTGGGATGACAAATGGTATTCCAAAGTTCAAGATATTTCTTTTTAGATTTAGGAATTTGTAGTCT
TTTAAGGTTAGAGGTTACTTAAAAGGATGAACAAATTTTTTATCCCATTCTATTTCTAGGAAGAATTTATA
ATCCGTACGTGTGACGGCTGCCATTAATTATAGTGCCCATTCATTTTTATTGGGAAAAAGTACTCATCCATT
ATTTCATTGGCACGGCAACCCAGTTTTAAATATTTTATAACAATAATAACATATGGAACCAAATTGTAACCT
TTATATCCCACAGACCCACACATTACACATCCAATAAAACTTGAGCCAAATTATATATTAGCGTTACTGAGT
ACTGACTAAAATATATTTTTAAAATATACTAAAATATTATTAAAAAAATATTAAAATAGTAAAATTATATT
AAATAGAAAATTTAATTTAATCAAAGAATACCAACTAAAACGTATAAAATGAGAAAATATAGGTATATAATA
TTGATGATTCCTTTTGATTTTTTTTTATGATCCGAAAATTCTTTGGCCATAAGAAGAGTAAATGAACAAT
TTAAACTAAGAAAATAAGTAAGTTGCTCCTATGTGATTAATATATAAAGTGAGATTTGAGCTGTTGATCTA
TATTATTGAATTAGATCAACGACTCAAAATGAAGGATAATTTTTTTAAAAAATCGCTTCCTGTTAATATTA
ATGCTTTAAAATTAAGCACATTAAACTTTAAAATAATGCACCTTTTTTTTTAATACTATTGACCTTGTTACA
TGTAGTATCTGAAGTCCAACAAAGTCAACATTGTCCCCACTGAGGCTCAAACCCGTGACCTCCCACTAGGGA
GAATCGCTTCATGCCGCTTGACCACAAGTCCTTTGGTAAAAATAATGCACCTTAAAGATGTAAACTTACGCA
TCTTCGATGAACTGACCACTTTGAGCTTGCAACTTATACTTTTTGAAGATAAGCTTGTAACTTATTATAAT
GGTCTATTAACATTAAAAAAAAAAAAAGTTTCACAATCAAATTATAATATTTGTAGCCAAATGAATTTA

-1228
CCGCGGGTGTGACTATTCAGGAATTTAAATACACTAAAGTTGGAGGGGTAGTACACTCAATACACTATTGCT
CATGACTTTTTTCTTCTTTTTTTTTAGATTAGCTAATATATTAATCCCAAATAGAAACGTTTACACCAAAG
TTCGAAAAAATGTTGTGTCATTTCTTACAGTTAGACACAAAAATAACATTTTTAGCTAAGTTACAGTAAACT
TGATTGGCAGACTGTTTCACAAATTGGGAGCTTGGATCCTTGAAGGAACTTACTGCTTTCTTAGAGTCATTA
ATGGTTTGGCCAAACATAGAAAAGATTAGTTGAGCAGTCTTGCACACTACTTGAGTAATCATCTCCATTCTT
CTACTTATTGACAATATTCTCTTATGAAAAAACACACTTGATCTTATATCAGTTAGGGATTTGACCGGTTTA
TTAAAGGATAGCCTACCAACTTTGTTGAACGACATATCATCATATCATGATTCAAAAGATGCTCTTTTTTAT
TGTCATATTTGTGGCACAGGATGAGTACAGTTTCGCATACACCATGATCATTTTTATCAAATCATACTCTAT
AAAACCCTGTCAAAGAAAAGAGAGGAAGAAACGAGAAGAAGAAACTCATCCAAGAAACAAGAGGAACATTAT
TGCTCATGATTAGATCGACTTGAACATGTACTAATGCCAATCTCAAATTACCTACATAGGTGTGTTAGACAA
ATATTTGTTAATTAGCTGATTGACTTAATGGATTTGACTAGTTGTTAACATTAATTGATTGTAGGAAATTG
TTTGGTAAATTAGTTGTTAGTTGATAGTTGATTACATGAAAATTACTTTCTCAAAAAGCTTATCGAAAAAA
CTATTTTGAACAGCTTTTTGAATTTTAACATTTTATAACAATAAGTTGTTACAAAAAGCTAATTAATCAAA
TACTCATATCCATTGTTTAACCATGTCAAACAACTAATAATAATTAAATAATTTGTTTTTAAAATATAAGTT
AAATTTAATTGATAAGCTAACTATATTACCAAACATACCGTAATATTTTCTTAACCGCGGTATGGGCTAAGA
TATGATTGTATACTATTTTTGTTGCGAGCATGATTAATACAGTAATACCATCATTTAAAAGTGGAAACCACA
TTCGCAGCTGTTTCCGAAAGCAAACAGCTAACATTTGCTAGGTTCTTACTTATGCATTAATCTGGGTTATAA
AATCCCC

+1
ATTTCCATGTTGGTGTGAACAACCACCTAAACCTAGCGTCTTCAACAATTCTACCCTACTATCATCCCCCAA
GACTTCCCCGACCA*GTAAATAACCCGCTTTCCTCTTTCAGTGATTTCTTCATTTGACTTTGCTATATATATA*
*TATAATCTGATCTGCTTTCATCTTTCAGTGATTTCTTCATTTGGATTTCTTCAG*GGAGGAGAAGG<u>ATG</u>

*FIG. 5*

SWEET POTATO MADS-BOX PROMOTER DIRECTING HIGH LEVEL EXPRESSION IN PLANT STORAGE ROOT

This application is a continuation of Patent Application No. PCT/KR2004/003052 filed Nov. 24, 2004 which designates the United States and claims priority of Korean Patent Application No. 2004-0067290 filed on Aug. 25, 2004.

FIELD OF THE INVENTION

The present invention relates to a MADS-box promoter directing high level expression in a plant storage root, an expression vector using the same and a transient assay method in a plant storage root using the same vector. More specifically, the present invention relates to a sweet potato MADS-box gene promoter sequence directing a high level expression in a plant storage root, a plasmid vector using the same and a transient assay method in a plant storage root using the same vector.

BACKGROUND ART

The molecular breeding technology of crops makes it possible to use the genes of all species as breeding materials and to regulate the effects of breeding minutely at the gene level instead of at the genome level as in the past. Therefore it is one of the core technologies leading into the next generation of agriculture.

In order to maximize the effects of such molecular breeding technologies of crops, the essential prerequisites are as follows:

1) the accumulation of a database of genes to represent various plants;
2) the establishment of transformation systems for various crops; and
3) the development of promoters that regulate the expression of foreign genes inserted into plants.

In foreign countries promoters regulating the expression of plant genes have been studied since the early 1980's. It was suggested that a promoter of cauliflower mosaic virus could induce high levels of gene expression in all kinds of plant tissues (Hohn et al., 1982, *Curr. Topics Microbiol. Immunol.* 96: 193-236).

Subsequently, the sequence of the promoter was identified (Odell et al., 1985, *Nature* 313:810-812). It was proved that the promoter could induce high levels of gene expression in plants (Sanders et al., 1987, *Nucleic Acids Res.* 15: 1543-58). Since then, CaMV 35S promoter (Patent NO.: JP1993192172-A1) has become the most universal promoter used in plants.

Since the identification of CaMV 35S, promoters expressing genes in specific plant tissues have been actively studied. The specific studies relating to the promoters expressing genes in specific plant tissues are as follows.

The Studies Relating to Seed Specific Promoters

Since seed specific promoters are expected to be highly useful in molecular breeding technologies for crops, the field of study relating to them is one of the fields that have been most actively studied concerning tissues specific promoters. Beta-phaseolin is the seed storage protein of French bean. The promoter of its gene has been cloned (Bustos et al., 1989, *Plant Cell* 1: 839-853). Then it was found that the UAS1 (−295~−109) part of the promoter is a necessary cis-element for seed specific expression (Bustos et al., 1991, *EMBO J.* 10: 1469-1479). After that it was reported that 68 bp (−64~+6) in UAS1 acts as a seed specific enhancer (van der Geest and Hall, 1996, *Plant Mol. Biol.* 32: 579-588).

In addition, it was found that B-box ABA-complex and RY/G complex are necessary for napin gene promoter (napA) to express a gene in seed tissue (Ezcurra et al., 1999, *Plant Mol. Biol.* 40: 699-709). Various seed specific promoters have been found, such as the promoter of storage protein glutelin gene (Glu-B1) in a rice plant (Washida et al., 1999, *Plant Mol. Biol.* 40: 1-12) and the promoter of trypsin/chymotrypsin inhibitor gene (TI) in a pea (Welham and Domoney, 2000, *Plant Sci.* 159: 289-299).

The Studies Relating to Flower Tissue Specific Promoters

It was found that 67 bp of chsA (chalcone synthase) gene promoter in Petunia is necessary to express a gene in the flower tissue (van der Meer et al., 1990, *Plant Mol. Biol.* 15: 95-109). It was also reported that the promoter of the tomato LAP (leucine aminopeptidase) gene is a flower tissue specific promoter and the region from bp −317 to −3 of the gene is a decisive factor in order to express a gene in the flower tissue (Ruiz-Rivero and Prat, 1998, *Plant Mol. Biol.* 36: 639-648).

The Studies Relating to Root Tissue Specific Promoters

The peroxidase gene promoter (prxEa) of *Arabidopsis thaliana* is the root tissue specific promoter and the regulating factor for tissue specific expression is in between bp −172 and −1 of the gene (Wanapu and Shinmyo, 1996, *Ann N.Y. Acad. Sci.* 782: 107-114). Recently another root specific promoter (Pyk10) of *Arabidopsis thaliana* has been reported and the regulating factor of the promoter has also been reported (Nitz et al., 2001, *Plant Sci.* 161: 337-346).

The Studies Relating to Potato Tuber Specific Promoters

A patatin gene is glycoprotein expressed in the potato tuber in large quantities and is related to the activity of lipid acyl hydrolase. A patatin gene promoter can regulate the potato tuber specific expression (Patent No. EP0375092, B1; Jefferson et al., 1990, *Plant Mol. Biol.* 14: 995-1006). The regulating factor located in bp −183 to −143 of the gene acts as a decisive factor for tuber specific expression induced by sugar (Liu et al., 1990, *Mol. Genl Genet.* 223: 401-406). Further, a nucleus protein has been reported as a trans-acting factor that regulates the tuber specific expression of the patatin promoter (Kim et al., 1994, *Plant Mol. Biol.* 26: 603-615).

Meanwhile, sporamin accounts for 60-80% of the total soluble proteins in the storage roots of a sweet potato. Therefore, various studies have been conducted in order to use the above gene promoter as a storage root specific promoter in sweet potato.

However, it has not been identified whether the promoter can induce expression of a gene in storage root yet. A high level of expression was found in the stalks, leaves and sieve tube tissues of a transgenic tobacco plant using the same promoter (Hattori et al., *Plant Mol. Biol.* 14: 595-604. 1990, Ohta et al., *Mol. Gen. Genet.* 1991, 225:369-378).

Therefore, despite the wide scope of studies relating to tissue specific promoters, a storage root specific promoter that is selectively functional in plant storage root has not been reported yet.

DISCLOSURE OF THE INVENTION

Technical Problem

In order to solve the above problems and needs, an object of the present invention is to provide the promoter DNA sequences directing high levels of expression of a gene in plant storage root.

Another object of the present invention is to provide a vector comprising the promoter DNA sequence directing high levels of expression of a gene in plant storage roots.

A still further object of the present invention is to provide the transient assay method for the expression of foreign genes in plant storage root using the same vector.

Technical Solution

In order to accomplish the above objects, the present inventors have cloned root- and storage root-specific promoter region of sweet potato MADS-box gene and developed promoter inducing high levels of expression of a gene in storage roots with the 5'-non translated region of the same gene. These inventors have subsequently induced transient expression in the storage roots of carrots and small radishes (*Raphanus Sativus* L.) and observed the high levels of activity of the promoter to perfect the present invention.

Therefore, the present invention provides the isolated DNA sequence of the root- and storage root-specific promoter region (SEQ ID NO:10) and the 5'-non translated region of sweet potato MADS-box gene (SEQ ID NO:13) as set forth in SEQ ID NO:1.

The above DNA sequence of the promoter region is derived from SEQ ID NO:12 which is the region of bp −1 to −2801 relative to the transcription initiation site of the sweet potato MADS-box gene in SEQ ID NO:1 as shown in FIG. 5.

The above non translated region comprises SEQ ID NO:13 which is the non translated region of bp +1 to +209 relative to the transcription initiation site of the sweet potato MADS-box gene in SEQ ID NO:1 as shown in FIG. 5. The non translated region can enhance the translation efficacy of a target gene introduced into the plant to induce high levels of expression of the target gene like the other reported 5'-non translated regions of plant.

In order to accomplish another object, the present invention provides an expression vector comprising the storage root-specific promoter and 5'-non translated region of the sweet potato MADS-box gene directing high levels of expression in plant storage roots.

The above storage root specific expression vector may be a transient expression vector that can transiently express foreign genes in plants. However, it may preferably be a binary vector that can permanently express foreign genes in transgenic plants. In the present invention, for example, a transformation using the transient expression vector was performed.

The binary vector can be any binary vector comprising the RB and LB of T-DNA that can transform the plant in the presence of the Ti plasmid of *Agrobacterium tumefaciens*. Preferably, it may be a binary vector frequently used in the related field such as the pBI101 (cat#: 6018-1, Clonetech, USA), pBIN (Genbank accession NO. U09365), pBI121, pBIN20 or BIBAC vector.

If the above expression vector for storage roots is a binary vector, plants can be transformed using the method of *Agrobacterium tumefaciens* (An, G. 1987, Plant Physiology) or particle bombardment (Lacorte et al., 1997, Plant Cell Reports).

The present invention provides a transient expression vector that can transiently express foreign genes in a plant.

Concerning the expression vector of the present invention for plant storage roots, the promoter and 5'-non translated region of MADS-box gene according to the present invention are located in front of the foreign gene in the pBI221 vector. The present invention provides the pSPmasds-3.0 and pSPmads-1.5(FIG. 6) prepared by inserting the promoter and 5'-non translated region of MADS-box gene according to the present invention into the vector (pBI221) including the GUS reporter gene. However, the GUS reporter gene is a foreign gene and may be replaced with other foreign genes as is deemed useful.

Further the present invention provides the storage root transformed transiently using the transient expression vector according to the present invention.

Plant storage root can be transiently transformed using expression vectors according to the present invention using the particle bombardment method (Lacorte et al., 1997, Plant Cell Reports). Expression vectors of the present invention for plant storage roots can transform the storage root regardless of the kind of crop. Examples of the crop may be carrot, small radish, etc.

In order to accomplish another object, the present invention provides a transient assay method that may induce high levels of expression of foreign genes transiently in plant storage roots using the expression vector of the present invention for plant storage root.

The above foreign gene may any gene that is intended to be expressed in large quantities in plant storage root. Furthermore, they are located next to the promoter and 5'-non translated region of the sweet potato MADS-box gene in the expression vector for plant storage root according to the present invention and may be expressed fused with the reporter genes if necessary.

The present invention provides PCR primers represented as SEQ ID NO: 2 and SEQ ID NO: 4 in order to clone the sweet potato MADS-box promoter.

The present invention provides PCR primers represented as SEQ ID NO: 6~SEQ ID NO: 9 in order to amplify the DNA fragment of the promoter comprising the sequence represented as SEQ ID NO: 1.

Advantageous Effects

The present invention relates to the promoter and 5'-non translated region of the MADS-box gene derived from sweet potato (*Ipomoea batatas*). The promoter and 5'-non translated region of the sweet potato MADS-box gene according to the present invention can induce plant root and storage root specific expression and particularly can induce high levels of expression in plant storage roots. Therefore the present invention may be useful for the development of transgenic plants to produce valuable materials in large quantities in plant storage roots.

BRIEF DESCRIPTION OF DRAWINGS

The above and other objects, features and other advantages of the present invention will be more clearly understood from the following detailed description taken in conjunction with the accompanying drawings, in which:

FIG. 5 shows sequences of promoter and 5'-non translated region of the sweet potato MADS-box gene according to the present invention. In FIG. 5, the first section from −2801 to −1229 is SEQ ID NO:11, the second section from −1228 to −1 is SEQ ID NO:10, the third section from +1 to +209 (excluding the start codon, ATG) is SEQ ID NO:13. The first and second sections (SEQ ID NOs: 11 and 10) together is SEQ ID NO: 12, the second and third sections (SEQ ID NOs: 10 and 13) together is SEQ ID NO:14, and all three sections (SEQ ID NOs: 11, 10 and 13) together is SEQ ID NO:1;

DETAILED DESCRIPTION OF PREFERRED EMBODIMENTS

The following examples will enable those skilled in the art to more clearly understand how to practice the present invention. It is to be understood that, while the invention has been described in conjunction with the preferred specific embodiments thereof, that which follows is intended to illustrate, not to limit the scope of the invention. Other aspects of the invention will be apparent to those skilled in the art to which the invention pertains.

EXAMPLE 1

Identification of a Gene Expressed Particularly in Plant Root and Storage Root

In order to find a gene expressed particularly in plant root and storage root, the present inventors performed Northern blot analysis with various sweet potato tissues. More specifically, ESTs of sweet potato (*Ipomoea batatas* cv. Jinhongmi) storage roots expressed at the early stage of development were analyzed (You et al., 2003, FEBS Letters, 536; 101-105).

Total RNA was isolated from leaf (Leaf-FRN), stem (Stem-FRN), petiole (Petiole-FRN) and root (FRN) of sweet potato at a non-storage root stage, leaf (Leaf-SR), stem (Stem-SR), petiole (Petiole-SR), root (FRES) and storage root (SR) of sweet potato at an early storage root stage, and root (FRLS) of sweet potato at a late storage root stage.

Figure 1:
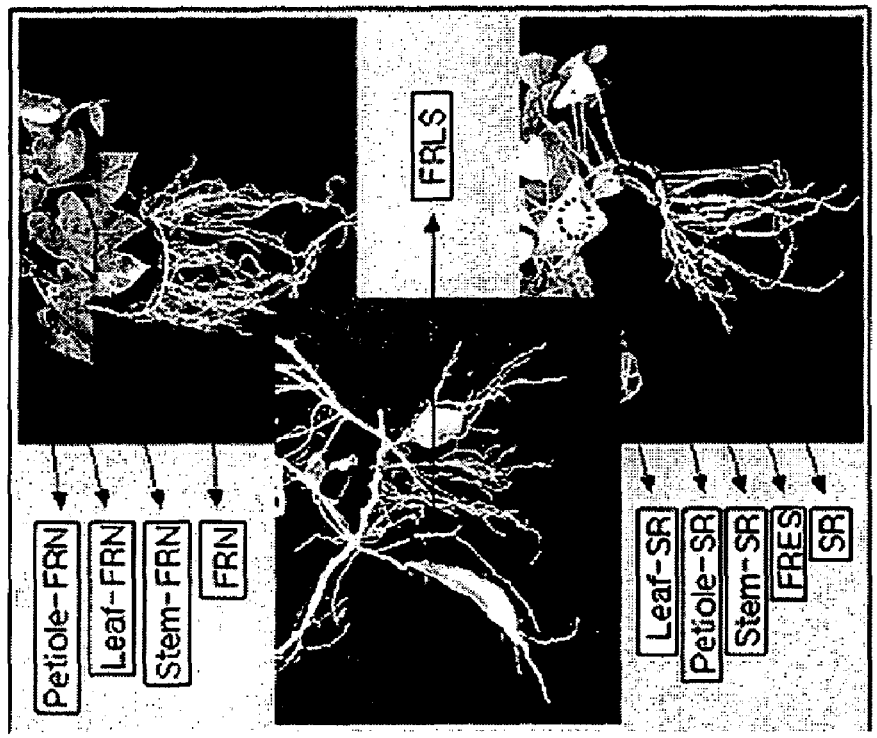
FIG. 1 shows tissues of sweet potato used in Northern blot analysis to analyze expression patterns of *Ipomoea batatas* MADS-box gene (ibMADS) in the present invention.

FRN means fibrous root of non-storage root stage and FRES means fibrous root of early storage root stage. Furthermore SR means Storage root (<1.5 cm in diameter) and FRLS means fibrous root of late storage root stage (FIG. 1).

Figure 2:
FIG. 2 shows the result of Northern blot analysis of ibMADS using sweet potato tissues shown in FIG. 1.

Using sweet potato ESTs as a probe, the extracted total RNA were analyzed by Northern blot analysis. As a result, sweet potato MADS-box gene was found to be expressed in root tissues at a non storage root stage and an early storage root stage of development. Furthermore, it was identified that the MADS-box gene was highly expressed in storage root tissues at a mature storage root stage (FIG. 2). However, it was not expressed in the other tissues of sweet potato. Therefore, the MADS-box gene is found to be expressed particularly in plant root and storage root tissues.

EXAMPLE 2

Cloning for the Promoter of the Sweet Potato MADS-Box Gene

In order to clone the promoter of the sweet potato MADS-box gene, sweet potato (*Ipomoea batatas* cv White Star) Genome Walker library was screened by PCR.

For the first PCR, Mads (124)R primer(SEQ ID NO: 2 in the Table 1) generated on the basis of the sweet potato (*Ipomoea batatas* cv. Jinhongmi) MADS-box cDNA sequence and adapter primer 1(SEQ ID NO: 3 in the Table 1) were used.

In the second PCR, Mads (94)R primer (SEQ ID NO: 4 in the Table 1) generated on the basis of the sweet potato (*Ipomoea batatas* cv. Jinhongmi) MADS-box cDNA sequence and nested adapter primer 2 (SEQ ID NO: 5 in the Table 1) were used. PCR was carried out according to the guide book of Universal Genome Walker Kit (Clonetech).

TABLE 1

| | | |
|---|---|---|
| Primers for the first PCR | 5'-ATCCTCCTAATTTCAACCTTGC CCCTC-3' | SEQ ID NO:2 |
| | 5'-GTAATACGACTCACTATAGGGC -3' | SEQ ID NO:3 |
| Primers for the second PCR | 5'-ATCCTTCTCCTCCCTATTTCTG GGATG-3' | SEQ ID NO:4 |
| | 5'-ACTATAGGGCACGCGTGGT-3' | SEQ ID NO:5 |

Figure 3:
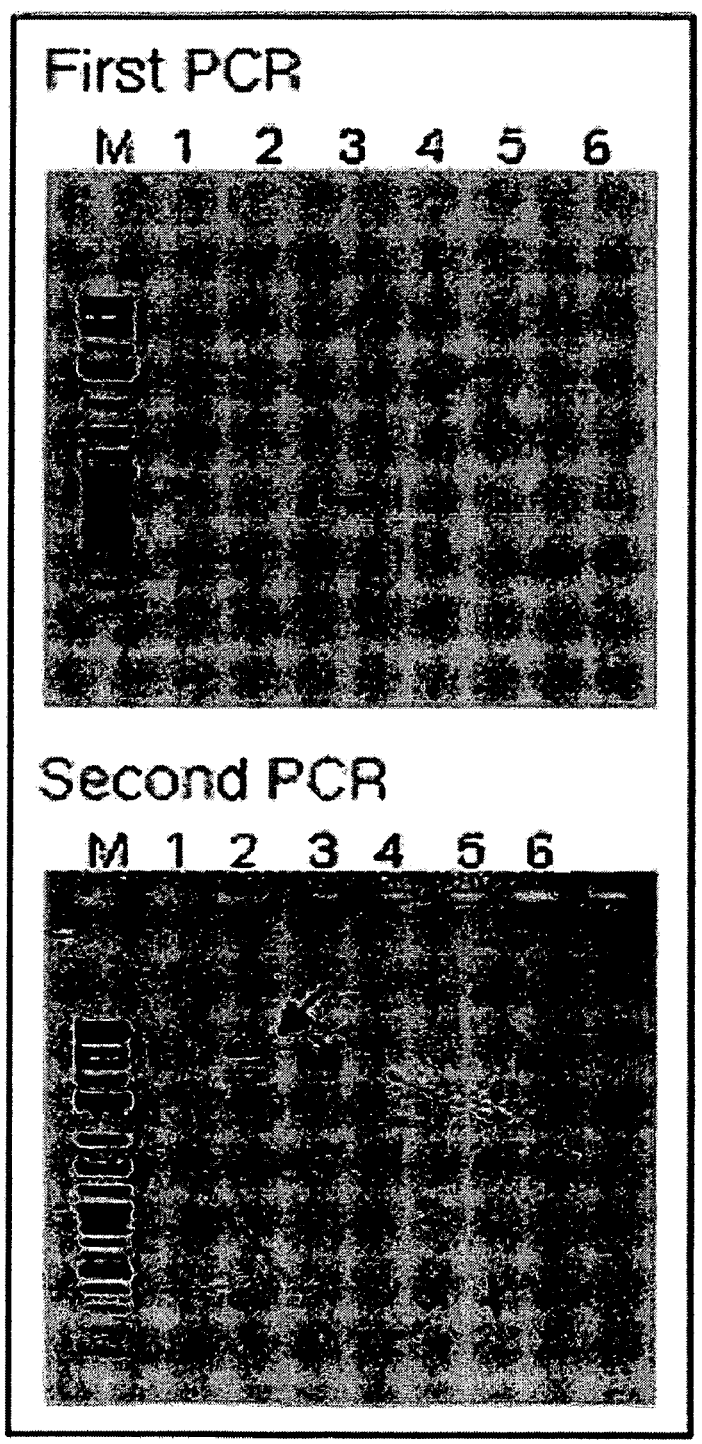
FIG. 3 shows a PCR process for cloning of the promoter according to the present invention.
Figure 4:
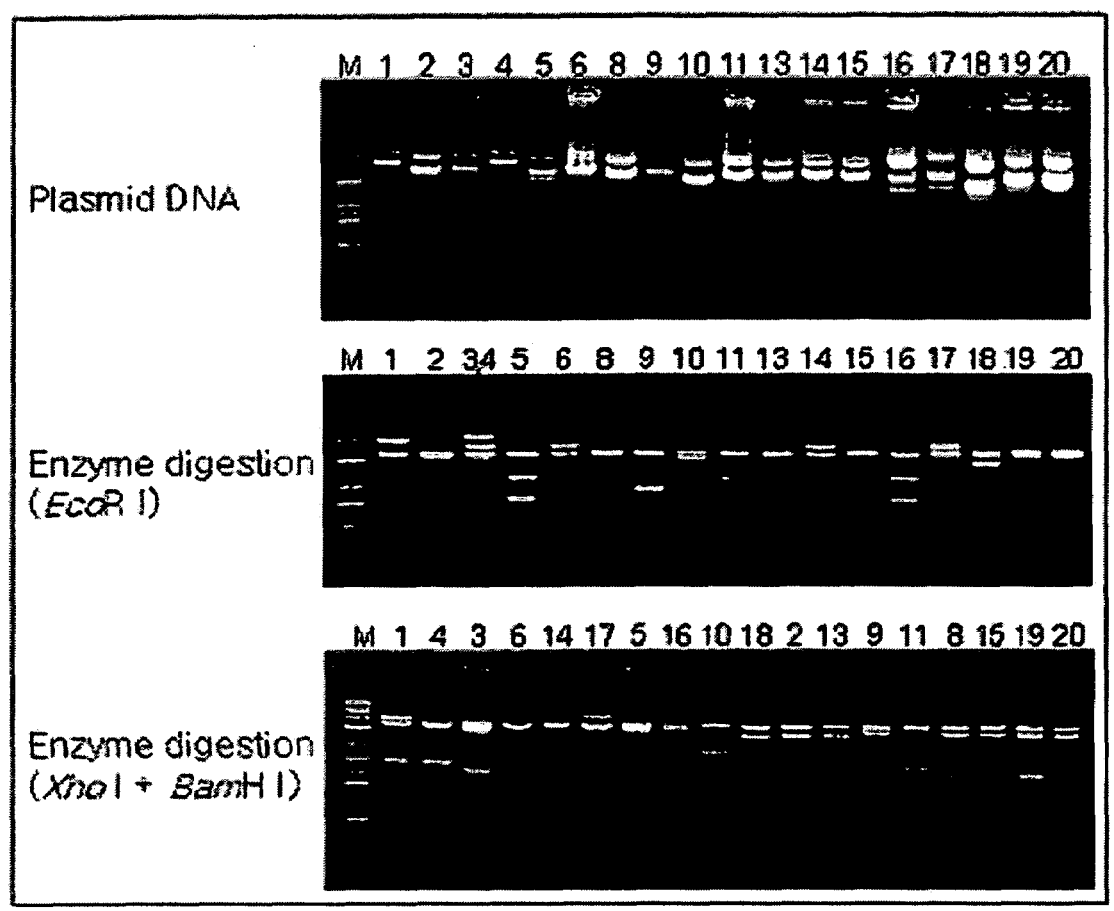
FIG. 4 shows the identification of promoter according to the present invention using restriction enzymes.

The result is presented in FIG. 3 and FIG. 4 that show electrophoresis of the first and second PCR products in the agarose gel. The No. 2 product (3-6 kb) of the second PCR products was eluted from the agarose gel and inserted into pCR-XL-TOPO vector using the TOPO XL PCR Cloning Kit (Invitrogen). Then, plasmids were extracted from 20 colonies of *E. coli* and identified by restriction enzymes (FIG. 4). Through sequencing of plasmids, it was identified that one of plasmids had homology with the 5' sequence of sweet potato (*Ipomoea batatas* cv. Jinhongmi) MADS-box cDNA (NO. 10 in FIG. 4). The total sequence of the cloned region (about 3 kb) was registered in NCBI GenBank (Accession no. AY655162).

FIG. 5 shows sequences of promoter and 5'-non translated region of sweet potato MADS-box gene according to the present invention. The start codon 'ATG' of protein synthesis is underlined and base 'A' of transcription initiation site is indicated '+1'. Though there is a putative intron (indicated with an italic letter) in the 5'-non translated region, the sequence of the intron region is different from the sequence of cDNA of sweet potato (*Ipomoea batatas* cv. Jinhongmi).

EXAMPLE 3

Construction of Vectors for Transient Expression of Plant Storage Root Specific Promoter The sweet potato MADS-box promoter and the 5'-non translated region cloned in example 2 were inserted in a pBI221 vector. In this case, two lengths of promoter regions were used. One was SEQ ID NO:12 which in combination with the 209 bp (SEQ ID NO:13) of the 5'-non translated region gave a 3,010 bp sequence. The other was SEQ ID NO:10 which in combination with the 209 bp (SEQ ID NO:13) of the 5'-non translated region gave a 1,437 bp sequence.

Figure 6:
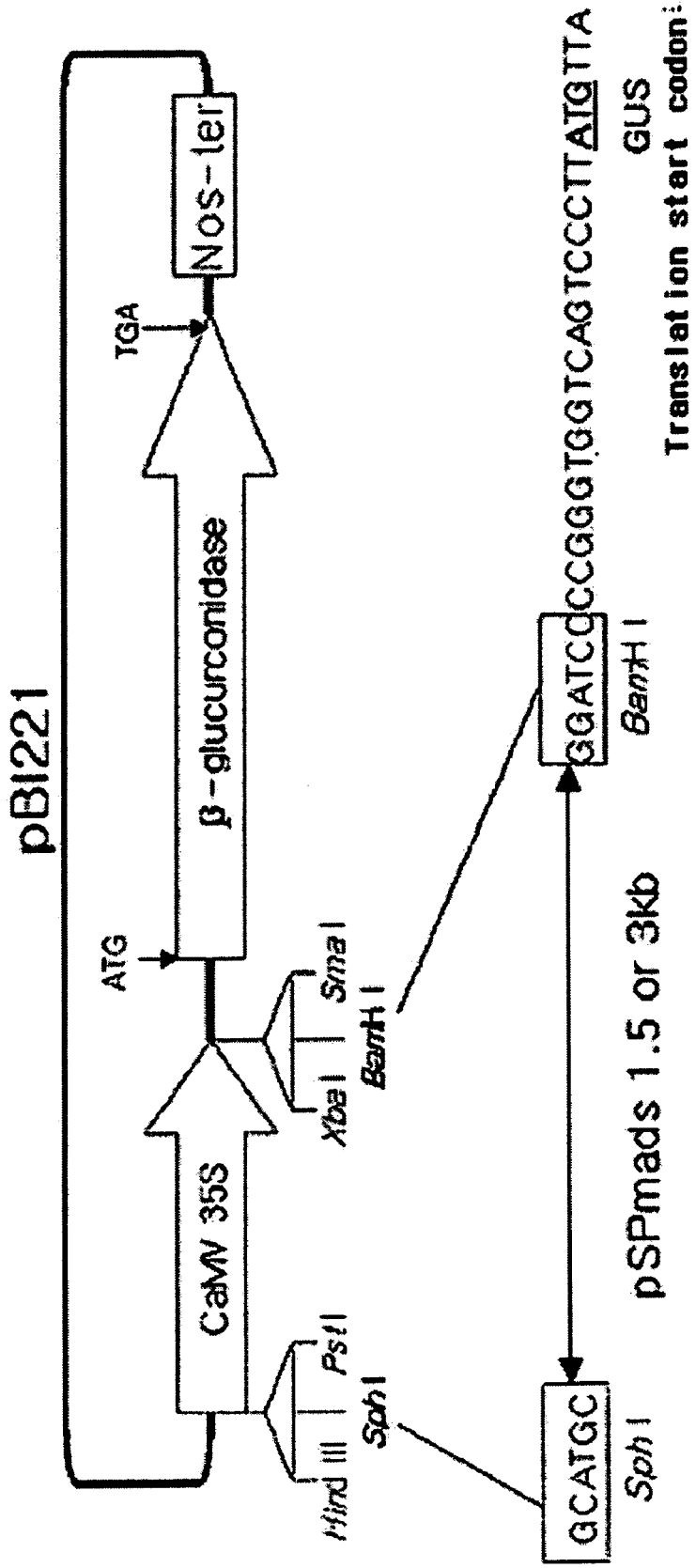
FIG. 6. shows a transient expression vector (hereinafter refeffed to pSPmads-1.5 or pSPmads-3.0) comprising promoter and 5'-non-translated regions of the sweet potato MADS-box gene according to the present invention. The 30 nucleotide sequence shown in FIG. 6 is SEQ ID NO:15.

The above 3,010 bp sequence and 1,437 bp sequence were amplified by PCR and restricted by SphI and BamHI. Then they were inserted into SphI and BamHI sites of pBI 221. The vectors were named pSPmads-3.0 and pSPmads-1.5 respectively (FIG. 6). The primers used in the above PCR are shown in Table 2 in detail.

In the PCR, after the process was conducted for 4 min at 94° C., the following cycling parameters were used; 5 cycles [94° C., 1 min; 60° C., 1 min; 72° C., 2 min and 30 s], 5 cycles [94° C., 1 min; 63° C., 1 min; 72° C., 2 min and 30 s], 20 cycles [94° C., 1 min; 66° C., 1 min; 72° C., 2 min and 30 s]. After that the process was carried out for 5 min at 72° C.

TABLE 2

| PCR Primers for 3,010 bp promoter | 5' primer<br>5'-CATGTCGACGGCTGGTTTCTAAG<br>ACAT-3' | SEQ ID NO:6 |
|---|---|---|
| | 3' primer<br>5'-GCTAGATCTCCTTCTCCTCCCTG<br>AAGAAATC-3' | SEQ ID NO:7 |
| PCR Primers for 1,437 bp promoter | 5' primer<br>5'-CATGCATGCCCGCGGGTGTGACT<br>ATT-3' | SEQ ID NO:8 |
| | 3' primer<br>5'-GCTAGATCTCCTTCTCCTCCCTG<br>AAGAAATC-3' | SEQ ID NO:9 |

EXAMPLE 4

Identification of the Activity of the Storage Root Specific Promoter by the Transient Assay Method In order to identify the activity of pSPmads-3.0 and pSPmads-1.5 vector, the transient assay method was carried out. More specifically, the storage roots of carrots and small radishes (*Raphanus Sativus* L.) in growth and enlargement stages were picked and washed. Then the storage roots were cut 5 mm thick crosswise and placed fully wet in Petri dishes for 4-5 hours at 4° C.

According to the method of Sanford et al. (1993, *Meth Enzymol* 217:485-509), DNA was mixed and coated with gold particles 1.0 μm in diameter. In this case, the following bombarding conditions were used; [1.0 μg DNA in density, 1,350 PSi helium gas in pressure and 6 cm from carrots or small radishes (*Raphanus Sativus* L.) in distance].

After bombarding, they were placed in the darkness for 24 hours at 25° C. and histochemical staining was carried out to identify the activity of GUS. In order to stain the cut storage root tissues of carrots or small radishes, they were soaked in the solution comprising 1 mM X-glu (5-bromo-4-chloro-3-indoly-β-glucuronide) dissolved in DMSO (dimethyl sulfoxide), 100 mM sodium phosphate (pH 7.0), 10 mM EDTA, 0.5 mM potassium ferricyanide, 0.5 mM potassium ferrocyanide and 0.1% Triton X-10, and reacted for 24 hours at 37° C.

After the solution was removed, cut storage root tissues were rinsed with 70% ethanol for 24 hours and then were placed in regularly changed 100% ethanol for a few days to remove the chlorophyll contained in the tissues.

Figure 7:
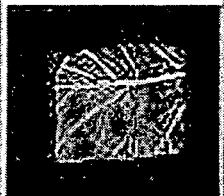
FIG. 7 shows the result of a transient assay using pSPmads-1.5 or pSPmads-3.0 according to the present invention.

As shown in FIG. 7, it was identified that pSPmads-3.0 was active in all carrot tissues with the exception of the secondary xylem tissue. And pSPmads-1.5 showed high levels of activity in all carrot tissues. Furthermore both the promoters showed high levels of activity in vascular cambium of carrot.

Meanwhile both pSPmads-3.0 and pSPmads-1.5 were highly active in all small radish tissues. However, when leaves of carrot or small radish were transformed with the above promoters, those promoters didn't show any activity (FIG. 7).

If the above results and the Northern blot assay result are considered together, it can be said that the activity of promoters according to the present invention is specific to plant storage roots and roots.

INDUSTRIAL APPLICABILITY

As described above, the present invention provides storage root specific promoters comprising promoter and 5'-non translated regions of sweet potato MADS-box genes. For a transient expression assay, the present invention provides the transient expression vector prepared by inserting the promoter into the pBI221. The transient assay shows that the promoter has a high level of activity particularly in the storage roots of carrots and small radishes. Therefore, it is identified that the promoter according to the present invention has activity specific to plant roots and storage roots.

The promoter according to the present invention is very useful for producing valuable proteins in the transformed storage root tissue, or for metabolic regulation of storage root tissue and for producing functional materials using transgenic plants.

SEQUENCE LISTING

<160> NUMBER OF SEQ ID NOS: 9

<210> SEQ ID NO 1
<211> LENGTH: 3013
<212> TYPE: DNA
<213> ORGANISM: Ipomoea batatas cv White Star -continued

<400> SEQUENCE: 1

```
ggctggtttc taagacattt tttggtttaa tccaaaccta attacaaata ttcccaacaa      60
gatcgaatga tctatggcta caaaccctat cccaacaaaa aactcacttt agtacatcaa     120
attaagtggc atgattattt tattttgttc gacaaagtag catcaaataa actacaaaaa     180
aaactacatc attacaaaaa gactaattat caggcatcaa tgttagtata tgggaggtgg     240
tgggttcgag cctcagtgga ggcgttgctg tctctttgtt cttcagtagg ttgagagagt     300
aatttatgaa cagatactac actgtaatag agtcagtagc aatcaaaaaa aaatttgttt     360
taataatatc ctaatattat attttctaa ccagtactat gctttcggct ttccagaagg     420
cagaagccta aaaaattcaa ttaagtttat aaactttaat ccacttgttt gagtaattga     480
gtatctttca gaacggttgt agatttaggt gggatgacaa atggtattcc aaagttcaag     540
atatttcttt ttagatttag gaatttgtag tcttttaagg ttagaggtta cttaaaagga     600
tgaacaaatt ttttatccca ttctatttct aggaagaatt tataatccgt acgtgtgacg     660
gctgccatta attatagtgc ccattcattt ttattgggaa aaagtactca tccattattt     720
cattggcacg gcaacccagt tttaaatatt ttataacaat aataacatat ggaaccaaat     780
tgtaaccttt atatcccaca gacccacaca ttacacatcc aataaaactt gagccaaatt     840
atatattagc gttactgagt actgactaaa atatatttt aaaatatact aaaatattat     900
taaaaaaata ttaaaatagt aaaattatat taaatagaaa atttaattta atcaaagaat     960
accaactaaa acgtataaaa tgagaaaata taggtatata atattgatga ttccttttga    1020
tttttttttt atgatccgaa aattctttgg ccataagaag agtaaatgaa caatttaaac    1080
taagaaaata agtaagttgc tcctatgtga ttaatatata aagtgagatt tgagctgttg    1140
atctatatta ttgaattaga tcaacgactc aaaatgaagg ataatttttt taaaaaatcg    1200
cttcctgtta atattaatgc tttaaaatta agcacattaa actttaaaat aatgcacctt    1260
tttttttaat actattgacc ttgttacatg tagtatctga agtccaacaa agtcaacatt    1320
gtccccactg aggctcaaac ccgtgacctc ccactaggga gaatcgcttc atgccgcttg    1380
accacaagtc ctttggtaaa aataatgcac cttaaagatg taaacttacg catcttcgat    1440
gaactgacca ctttgagctt gcaacttata cttttttgaa gataagcttg taacttatta    1500
taatggtcta ttaacattaa aaaaaaaaaa agtttcacaa tcaaattata atatttgtag    1560
ccaaatgaat ttaccgcggg tgtgactatt caggaattta aatacactaa agttggaggg    1620
gtagtacact caatacacta ttgctcatga ctttttttctt cttttttttt tagattagct    1680
aatatattaa tccaaatag aaacgtttac accaaagttc gaaaaaatgt tgtgtcattt    1740
cttacagtta gacacaaaaa taacatttttt agctaagtta cagtaaactt gattggcaga    1800
ctgtttcaca aattgggagc ttggatcctt gaaggaactt actgctttct tagagtcatt    1860
aatggtttgg ccaaacatag aaaagattag ttgagcagtc ttgcacacta cttgagtaat    1920
catctccatt cttctactta ttgacaatat tctcttatga aaaaacacac ttgatcttat    1980
atcagttagg gatttgaccg gtttattaaa ggatagccta ccaactttgt tgaacgacat    2040
atcatcatat catgattcaa aagatgctct tttttattgt catatttgtg gcacaggatg    2100
agtacagttt cgcatacacc atgatcattt ttatcaaatc atactctata aaaccctgtc    2160
aaagaaaaga gaggaagaaa cgagaagaag aaactcatcc aagaaacaag aggaacatta    2220
ttgctcatga ttagatcgac ttgaacatgt actaatgcca atctcaaatt acctacatag    2280
```

-continued

```
gtgtgttaga caaatatttg ttaattagct gattgactta atggatttga ctagttgtta    2340
acattaattg attgtaggaa attgtttggt aaattagttg ttagttgata gttgattaca    2400
tgaaaattac tttctcaaaa agcttatcga aaaaactatt ttgaacagct ttttgaattt    2460
taacatttta taacaataag ttgttacaaa aagctaatta atcaaatact catatccatt    2520
gtttaaccat gtcaaacaac taataataat taaataattt gttttttaaaa tataagttaa    2580
atttaattga taagctaact atattaccaa acataccgta atattttctt aaccgcggta    2640
tgggctaaga tatgattgta tactattttt gttgcgagca tgattaatac agtaatacca    2700
tcatttaaaa gtggaaacca cattcgcagc tgtttccgaa agcaaacagc taacatttgc    2760
taggttctta cttatgcatt aatctgggtt ataaaatccc catttccatg ttggtgtgaa    2820
caaccaccta aacctagcgt cttcaacaat tctaccctac tatcatcccc caagacttcc    2880
ccgaccagta aataacccgc tttcctcttt cagtgatttc ttcatttgac tttgctatat    2940
atatatataa tctgatctgc tttcatcttt cagtgatttc ttcatttgga tttcttcagg    3000
gaggagaagg atg                                                      3013
```

```
<210> SEQ ID NO 2
<211> LENGTH: 27
<212> TYPE: DNA
<213> ORGANISM: Artificial Sequence
<220> FEATURE:
<223> OTHER INFORMATION: Primer for PCR

<400> SEQUENCE: 2
atcctcctaa tttcaacctt gccccctc                                       27

<210> SEQ ID NO 3
<211> LENGTH: 22
<212> TYPE: DNA
<213> ORGANISM: Artificial Sequence
<220> FEATURE:
<223> OTHER INFORMATION: Primer for PCR

<400> SEQUENCE: 3
gtaatacgac tcactatagg gc                                             22

<210> SEQ ID NO 4
<211> LENGTH: 27
<212> TYPE: DNA
<213> ORGANISM: Artificial Sequence
<220> FEATURE:
<223> OTHER INFORMATION: Primer for PCR

<400> SEQUENCE: 4
atccttctcc tccctatttc tgggatg                                        27

<210> SEQ ID NO 5
<211> LENGTH: 19
<212> TYPE: DNA
<213> ORGANISM: Artificial Sequence
<220> FEATURE:
<223> OTHER INFORMATION: Primer for PCR

<400> SEQUENCE: 5
actatagggc acgcgtggt                                                 19

<210> SEQ ID NO 6
<211> LENGTH: 27
<212> TYPE: DNA
<213> ORGANISM: Artificial Sequence
```

```
<220> FEATURE:
<223> OTHER INFORMATION: Primer for PCR

<400> SEQUENCE: 6
catgtcgacg gctggtttct aagacat                                    27

<210> SEQ ID NO 7
<211> LENGTH: 31
<212> TYPE: DNA
<213> ORGANISM: Artificial Sequence
<220> FEATURE:
<223> OTHER INFORMATION: Primer for PCR

<400> SEQUENCE: 7
gctagatctc cttctcctcc ctgaagaaat c                               31

<210> SEQ ID NO 8
<211> LENGTH: 26
<212> TYPE: DNA
<213> ORGANISM: Artificial Sequence
<220> FEATURE:
<223> OTHER INFORMATION: Primer for PCR

<400> SEQUENCE: 8
catgcatgcc cgcgggtgtg actatt                                     26

<210> SEQ ID NO 9
<211> LENGTH: 31
<212> TYPE: DNA
<213> ORGANISM: Artificial Sequence
<220> FEATURE:
<223> OTHER INFORMATION: Primer for PCR

<400> SEQUENCE: 9
gctagatctc cttctcctcc ctgaagaaat c                               31
application no. 11/153,023
1
```

What is claimed is:

1. An isolated promoter directing expression of a gene in plant storage roots comprising a nucleic acid molecule having SEQ ID NO: 10.

2. The isolated promoter of claim 1, and further comprising SEQ ID NO: 11 at the 5' end of SEQ ID NO:10.

3. The isolated promoter of claim 1, wherein the nucleic acid molecule is SEQ ID NO: 12.

4. The isolated promoter of claim 1, wherein the nucleic acid molecule is operably linked at the 3' end to SEQ ID NO:13.

5. The isolated promoter of claim 2, wherein the nucleic acid molecule is operably linked at the 3' end to SEQ ID NO:13.

6. The isolated promoter of claim 4, wherein the nucleic acid molecule is SEQ ID NO: 14.

7. The isolated promoter of claim 5, wherein the nucleic acid molecule is SEQ ID NO: 1.

8. A transient expression vector containing the isolated promoter of claim 6.

9. A transient expression vector containing the isolated promoter of claim 7.

10. A plant transformation binary vector containing the isolated promoter of claim 6.

11. A plant transformation binary vector containing the isolated promoter of claim 7.

12. An *Escherichia coli* cell containing the transient expression vector of claim 8.

13. An *Escherichia coli* cell containing the transient expression vector of claim 9.

14. An *Escherichia coli* cell containing the plant transformation binary vector of claim 10.

15. An *Escherichia coli* cell containing the plant transformation binary vector of claim 11.

16. A transgenic plant containing the plant transformation binary vector of claim 10.

17. A transpenic plant containing the plant transformation binary vector of claim 11.

18. The isolated promoter of claim 1, wherein the nucleic acid molecule is cloned using PCR primers of SEQ ID NO:2 and SEQ ID NO:4.

19. The isolated promoter of claim 2, wherein the nucleic acid molecule is cloned using PCR primers of SEQ ID NO:2 and SEQ ID NO:4.

20. The isolated promoter of claim 4, wherein the nucleic acid molecule is amplified using PCR primers of SEQ ID NO:8 and SEQ ID NO:9.

21. The isolated promoter of claim 5, wherein the nucleic acid molecule is amplified using PCR primers of SEQ ID NO:6 and SEQ ID NO:7.

22. An isolated nucleic acid molecule selected from the group consisting of:

(a) SEQ ID NO:1;
(b) SEQ ID NO:10;
(c) SEQ ID NO:12; and
(d) SEQ ID NO:14; wherein the nucleic acid molecule directs expression of a gene in plant storage-roots.

23. A vector consisting of vector nucleic acid and a nucleic acid molecule consisting of a sequence selected from the group consisting of:

(a) SEQ ID NO:1;
(b) SEQ ID NO:10;
(c) SEQ ID NO:12 and
(d) SEQ ID NO:14; wherein the nucleic acid molecule directs expression of a gene in plant storage-roots.

* * * * *